United States Patent
Harding

(10) Patent No.: US 7,583,783 B2
(45) Date of Patent: Sep. 1, 2009

(54) X-RAY COMPUTER TOMOGRAPH AND METHOD FOR EXAMINING A TEST PIECE USING AN X-RAY COMPUTER TOMOGRAPH

(75) Inventor: Geoffrey Harding, Hamburg (DE)

(73) Assignee: GE Homeland Protection, Inc., Newark, CA (US)

( * ) Notice: Subject to any disclaimer, the term of this patent is extended or adjusted under 35 U.S.C. 154(b) by 0 days.

(21) Appl. No.: 11/625,429

(22) Filed: Jan. 22, 2007

(65) Prior Publication Data

US 2007/0153970 A1    Jul. 5, 2007

(51) Int. Cl.
*A61B 6/00* (2006.01)
(52) U.S. Cl. ............................................. 378/4; 378/86
(58) Field of Classification Search .................. 378/4, 378/57, 86
See application file for complete search history.

(56) References Cited

U.S. PATENT DOCUMENTS

| | | | | |
|---|---|---|---|---|
| 4,887,285 A | * | 12/1989 | Harding et al. | 378/88 |
| 5,265,144 A | * | 11/1993 | Harding et al. | 378/86 |
| 5,319,547 A | | 6/1994 | Krug et al. | |
| 5,414,623 A | * | 5/1995 | Lu et al. | 382/131 |
| 5,602,893 A | * | 2/1997 | Harding | 378/86 |
| 5,717,733 A | * | 2/1998 | Kurbatov et al. | 378/71 |
| 6,122,344 A | * | 9/2000 | Beevor | 378/88 |
| 6,363,136 B1 | | 3/2002 | Flisikowski et al. | |
| 6,693,988 B2 | | 2/2004 | Harding | |
| 6,744,845 B2 | * | 6/2004 | Harding et al. | 378/16 |
| 6,751,288 B1 | | 6/2004 | Hessler | |
| 2001/0050970 A1 | * | 12/2001 | Haar | 378/19 |
| 2003/0031295 A1 | * | 2/2003 | Harding | 378/86 |
| 2006/0153328 A1 | * | 7/2006 | Schlomka et al. | 378/4 |

(Continued)

FOREIGN PATENT DOCUMENTS

DE    10009285 A1    8/2001

(Continued)

OTHER PUBLICATIONS

Bushberg, The AAPM/RSNA Physics Tutorial for Residents, Imaging & Therapeutic Technology, vol. 18, No. 2, 1998, pp. 457-468.*

(Continued)

*Primary Examiner*—Edward J Glick
*Assistant Examiner*—Alexander H Taningco
(74) *Attorney, Agent, or Firm*—Global Patent Operation

(57) ABSTRACT

An x-ray computer tomograph, having an x-ray source that generates a fan beam of x radiation and having a two-dimensional energy-resolving detector array, both of which are situated on opposite sides of a gantry so that the x-ray radiation passes completely through a test region. A row of detector elements is situated in the plane of the fan beam and is adjoined in at least one direction perpendicular to the fan beam by several additional rows of detector elements. During the measurement, no secondary collimator is positioned between the test region and the detector array. The following equation applies for the width (B) of the detector elements: $B=Z_P*\arcsin(q_{max}*\lambda)$, where $q_{max}$ is a pulse transmission, $\lambda$ is a wavelength of the x radiation, and $Z_P$ is the distance of the measurement point from the detector.

9 Claims, 2 Drawing Sheets

U.S. PATENT DOCUMENTS

Figure 1:
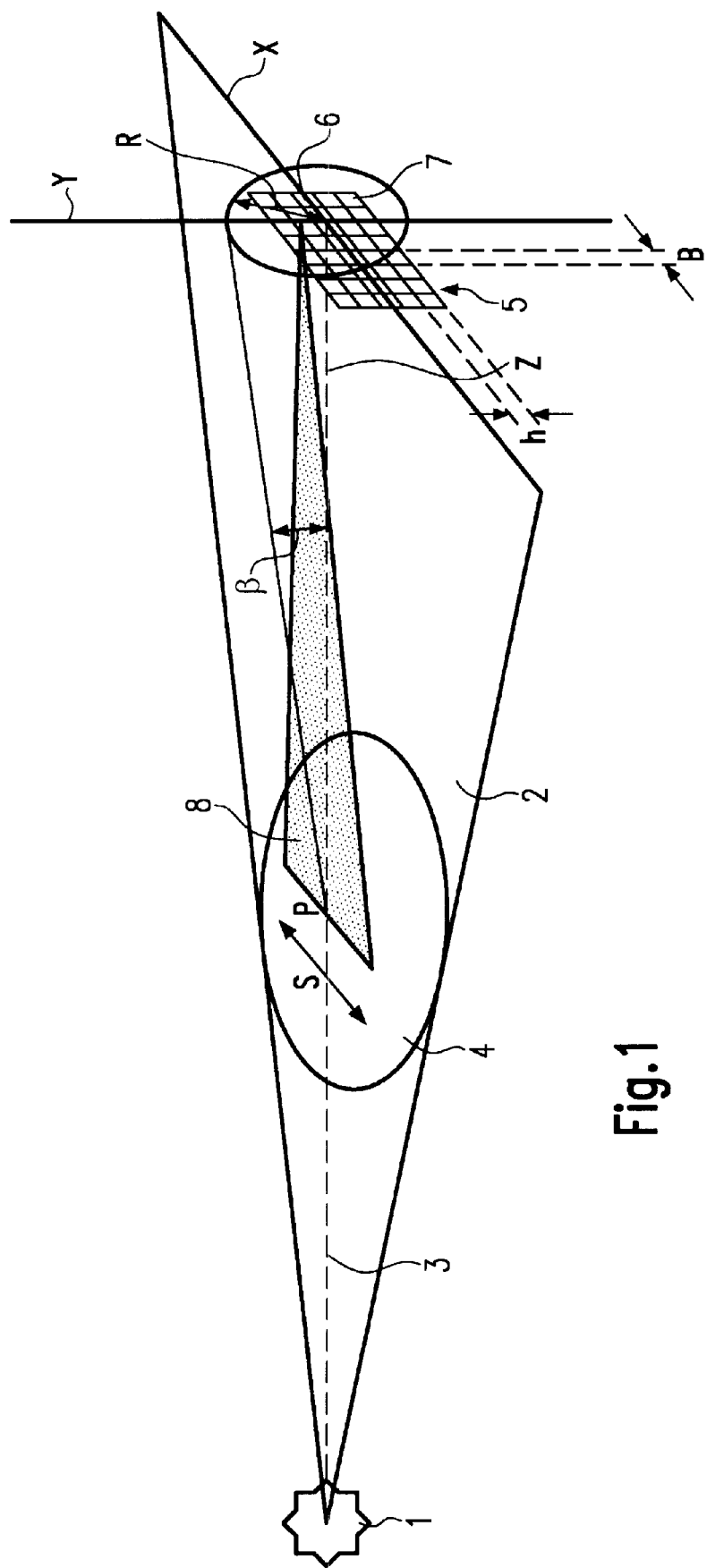

2007/0019782 A1* 1/2007 Van Stevendaal et al. ...... 378/6

FOREIGN PATENT DOCUMENTS

WO     WO02082065 A    10/2002

OTHER PUBLICATIONS

Johns et al., Measurement of coherent x-ray scatter from factors for amorphos materials using diffractometers, Physics in Medicine and Biology, 49, 2004, pp. 5233-5250.*

Van Stevendaal U et al:"A reconstruction algorithm for coherent scatter computed tomography based on filtered back-projection" Medical Physics, American Institute of Physics Bd. 30 Nr. Sep. 9, 2003.

Schlomka J-P et al:"Coherent Scatter Computed Tomography: a novel medical imaging technique" Proceedings of the Spie, Bd.5030, Feb. 16, 2003.

Schneider SM et al:"Coherent Scatter Computed Tomography Applying a Fan-Beam Geometry" Proceedings of the Spie, Bd.4320 Feb. 18, 2001.

* cited by examiner

X-RAY COMPUTER TOMOGRAPH AND METHOD FOR EXAMINING A TEST PIECE USING AN X-RAY COMPUTER TOMOGRAPH

The invention concerns an x-ray computer tomograph, having an x-ray source that generates a fan beam and having a two-dimensional energy-resolving detector array, both of which are situated on a gantry. The invention also concerns a method for examining a test piece using an x-ray computer tomograph.

DE 10 009,285 A1 has disclosed a computer tomograph for detecting the pulse transmission spectrum in a test region. In it, an x-ray source equipped with a primary collimator is situated on a gantry that can be rotated around one axis and generates a fan beam. Opposite from the x-ray source, a detector array is provided, which is likewise attached to the gantry and is used for detecting the x-rays passing through a test region. Between the test region and the detector array, a secondary collimator is provided, which only permits x radiation from a certain scattering voxel in the test region to pass through to an associated column of the detector array, Based on the scattered data obtained and the measured primary radiation in the plane of the fan beam, an iterative algebraic reconstruction technique (ART) is used to execute a reconstruction for each scattering voxel in the test region through which a primary beam passes, in conjunction with the pulse transmission spectrum. The pulse transmission spectrum is characteristic of the material in the relevant scattering voxel and thus provides information about its physical composition. But a computer tomograph of this kind and the method executed with it both suffer from significant disadvantages. First, the computer tomograph is rendered significantly more expensive by the use of a secondary collimator. Second, the leakage flux is reduced since part of the scattered x-ray quanta is absorbed at the secondary collimator, thus requiring a higher tube output or a longer testing time. Third, the secondary collimator itself constitutes a scattering source so that particularly with increasing photon energy, "smearing effects" occur in the measured pulse transmission spectrum.

The object of the invention, therefore, is to overcome the above-mentioned disadvantages.

The object is obtained by means of an x-ray computer tomograph with the defining characteristics of claim 1. By means of the two-dimensional energy-resolving detector array it is possible to determine the coherent scattered radiation from only a single arbitrarily selected scattering voxel, without having to position a secondary collimator between the detector array and the test piece to be examined. This is possible if the width of each individual detector element of the detector array in the x direction fulfills the condition $B=Z_P * \arcsin(q_{max}*\lambda)$. As a result, the coherent radiation is only produced to any appreciable degree in a very narrow angular range around the incidence direction of the x radiation. This width corresponds to a "strip" of $Z_P*\beta$, where $Z_P$ is the distance of the scattering point from the coordinate origin and $\beta=2\arcsin(q_{max}*\lambda)$, where $q_{max}$ is the maximum pulse transmission and $\lambda$ is the wavelength of the x radiation used. In practice, it therefore turns out that the width of a detector element must be less than or equal to $0.5*Z_P*\beta$. This results in the above-mentioned condition for the width of a detector element. It is thus possible here to use the known mathematical method ART to deduce what material is present in the associated scattering voxel. By eliminating the secondary collimator, the leakage flux is increased so that a test piece requires less tube output and/or less testing time. In addition, there is also no undesirable background of scattered radiation originating from leaves of the secondary collimator. Finally, an x-ray computer tomograph according to the invention is also less expensive than its prior counterpart equipped with a secondary collimator since on the one hand, material costs can be saved and on the other hand, the gantry is required to move significantly less mass during its rotation, which permits the use of less expensive drive units and bearings.

In an advantageous modification of the invention, the pulse transmission spectrum lies between 0.2 and 2 $nm^{-1}$. This is the range that includes the molecular structure functions of the materials that are of interest in the security field—for example, in baggage security checks at airports. The peak data and the intensity of the molecular structure functions for these materials are negligible above this range. In another advantageous modification of the invention, the energy of the x radiation lies between 100 and 500 keV. Such a high-energy x radiation broadens the testing region, both in security checks and in nondestructive analysis. In addition, this energy also has a positive impact on the required size of the individual detector elements of the detector array.

In another advantageous modification of the invention, the detector array is situated on a circumference surface of a cylinder around a center axis extending through the x-ray source, perpendicular to the fan beam. This makes it possible to use known detector array apparatuses that are situated on a gantry. As a result, not all the parts of the known x-ray computer tomograph have to be totally redesigned.

In another advantageous modification of the invention, the height h of the detector elements corresponds to the equation:

$$h = 0.2 * \arcsin(q_{max}*\lambda)*Z_P.$$

The detector resolution thus produced achieves an acceptable detector element height at very high x-ray energies and a conventional distance of the measuring point from the detector. It is advantageous if a pixelated detector array is used as the detector array, which is equipped with from 5 to 50 detector elements in the direction of the y axis. preferably 15 detector elements.

The object is also attained by means of a method with the defining characteristics of claim 7. In this method, a locally resolved measurement of coherent x radiation scattered forward by the test piece is performed without a secondary collimator being positioned between the test piece and the detector array. This makes it possible. through an unambiguous and simple deduction, to identify the material that is contained in the scattering voxel in question. According to the invention, the main component of the scattered signal is obtained based on data from detector elements that lie in an angular range of $$\beta=2*\arcsin(q_{max}*\lambda)$$

around the line of sight between the scattering voxel and the x-ray source. This assures that the detector picks up the majority of the coherently scattered x-ray quanta. In this case, carrying out the method according to the invention yields the same advantages that have already been described above in relation to the x-ray computer tomograph according to the invention.

In another advantageous modification of the invention, in order to record the scattered data, the gantry is rotated around an axis that is perpendicular to the plane of the fan beam. If scattered radiation from other scattering voxels strikes a detector element during an exposure without rotation of the gantry, then this is compensated for by the rotation since this causes a continuous succession of different partial beams to pass through the scattering voxel. The scattered radiation coming from the scattering voxel thus changes constantly, enabling a deduction based on the large amount of data that are obtained during the rotation of the gantry.

Other details and advantages of the invention are the subject of the remaining dependent claims or are explained in detail in conjunction with the exemplary embodiment shown in the drawings.

Figure 2:
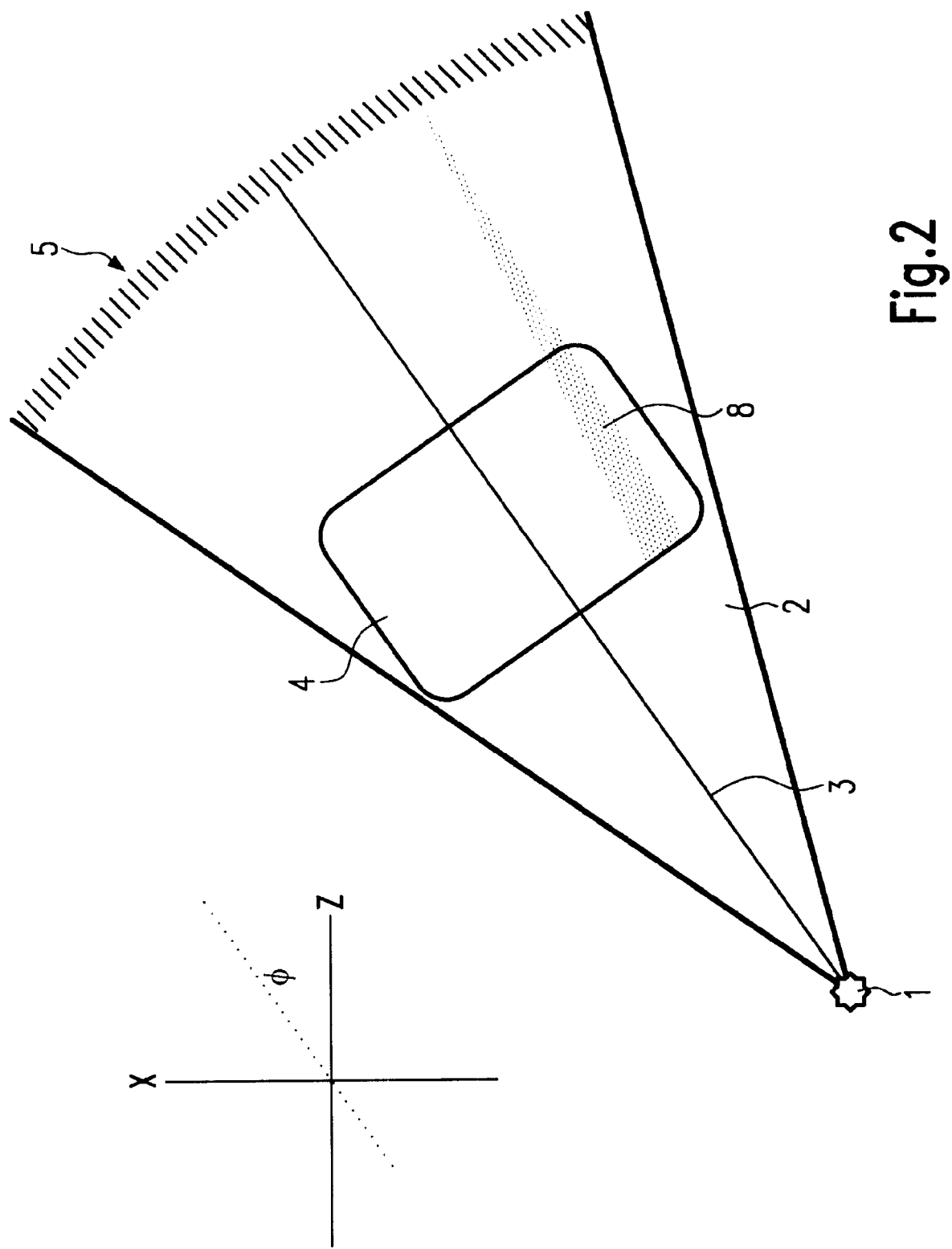

FIG. 1 is a perspective, schematic view of an x-ray computer tomograph according to the invention and FIG. 2 is a view to perpendicular to the fan beam of the x-ray computer tomograph from FIG. 1.

FIG. 1 shows the schematic design of an x-ray computer tomograph according to the invention in a very simplified fashion. In computer tomography using coherently scattered x-ray quanta, locally resolved diffraction patterns can be reconstructed from the scattered and detected x radiation. To this end, a fan beam 2 is used, which is produced by an x-ray source 1. The fan beam 2 is usually generated by means of a slit diaphragm serving as a primary collimator (not shown). The beam passes completely through the entire width of the test piece 4. In conventional and known testing methods, a secondary collimator is positioned between the test piece 4 and a detector array 5 and only permits scattered radiation from a certain region of the test piece 4, i.e. the scattering voxel S, to strike a certain element of the detector array 5. This usually achieves angular resolutions $\alpha$ in the region of $10^{-2}$ rad in the scanning plane, i.e. the plane of the fan beam 2 (the XZ plane in the example shown).

The molecular structure functions of the materials that are of interest in the field of security only lie in a range of pulse transmission $q_{max}$ of 0.2 to 2 $nm^{-1}$. In the following, when calculating the data that are significant to the x-ray computer tomograph according to the invention, reference will be made, for example, to the security field as practiced, for example, in the monitoring of containers in seaports and at airports. Other applications, for example the testing of welded seams in wheel rims or the nondestructive analysis of materials, would yield different values.

Above the indicated pulse transmission value $q_{max}$ of 2 $nm^{-1}$, only negligible peak data are obtained and the intensity of in the molecular structure function is likewise negligible. This value of the pulse transmission $q_{max}$ at each individual photon energy E corresponds to a particular angle $\beta$ of coherent scattered radiation. In this case, both of the following equations apply:

$$E*\lambda=1.24 \text{ keV nm}^{-1}$$

and $$\beta=2*\arcsin(q_{max}*\lambda).$$

If one takes into account the value of the angular resolution $\alpha$ of $10^{-2}$ rad indicated above for a conventional x-ray computer tomography then $\beta$ corresponds to an energy of the x-ray quanta of approximately 500 keV. This means that the electrons producing the x-ray quanta must be in the relativistic range since their static energy $E_0$ is 511 keV. At the photon energy indicated, the main portion of the scattered signal from a scattering voxel S stems from the line of sight 3 between the detector element and the x-ray source 1. By contrast, the contribution to coherent scattering of a material from a scattering voxel S situated on the line of sight 3 of an adjacent detector element is negligibly small. For this reason, it is no longer necessary to insert a secondary collimator equipped with leaves between the test piece 4 and the detector array 5.

The detector array 5 has a series of elements in a two-dimensional structure. It is manufactured out a material that has the capacity for energy-resolving detection, for example CdZnTe. The detector elements of the detector array 5 are situated on a circumference surface of a cylinder. The axis of the cylinder circumference passes through the x-ray source 1 and extends parallel to the y axis, i.e. perpendicular to the fan beam 2. The dashed line indicates the Z axis, which in the instance shown. corresponds to the line of sight 3 between the detector element—which is situated at the coordinate origin—and the x-ray source 1.

For the sake of clarity. Only some of the individual detector elements of the entire detector array 5 are shown. The detector array 5 has rows that extend parallel to the x axis and columns that extend parallel to the y axis, The primary radiation elements 6 are situated on the x axis and are used to detect x radiation coming directly from the x-ray source 1 and passing through the test piece 4, i.e. radiation that has not been scattered. By contrast, the rows situated outside the x axis—the scattered radiation elements 7—are used to detect only x radiation that has undergone a coherent scattering in the scattering voxel S.

If one assumes that the width B of a "strip" an object that emits coherent scattered radiation into a particular detector column is $\pm Z_P*\beta$, then this fulfills the condition according to the invention for the spatial resolution of the detector elements in their width B in the x direction, making it possible to eliminate a secondary collimator. The width B of each detector element must be less than $0.5*Z_P*\beta$, where $\beta=2*\arcsin(q_{max}*\lambda)$. At such widths of the detector elements, the coherent scattered radiation coming from an object point strikes only a single detector element and therefore permits an exact conclusion to be drawn as to the material that is present in this region.

The whole detector array 5 extends far enough in the x direction to detect the entire fan beam 2 passing through the test piece 4. In the direction of the y axis, i.e. with regard to the detector columns, 50 detector elements are usually sufficient since the coherent scattered radiation decreases in intensity as scattering angles increase, Due to the above-mentioned scattering angle-dependent intensity of the coherently scattered x-ray quanta, the coherently scattered x radiation from a scattering voxel S around a certain observation point P causes significant scattered radiation to be detected only in the above-indicated scattering angle range of up to $\beta$. Starting from the observation point P, this generates a cone in the region of which coherently scattered x-ray quanta from the scattering voxel S are detected in the detector array 5, Due to the approximation that occurs in small angles, the radius R of this region is proportional to the product $\beta*Z_P$ for small angles, where $Z_P$ represents the coordinates of the observation point P in relation to the origin of the coordinate system, Based on known x-ray computer tomographs, this distance $Z_P$ is assumed to be approximately 2 m, thus yielding a radius R of approximately 1 cm. The detector resolution depends on this radius R P The more detector elements in a column of the detector array 5 are situated within this radius A, the finer resolution is. The detector resolution achieved is R/N, where N must be greater than 10 in order to obtain reasonable results. Good results are obtained for N between 10 and 50; preferably N is selected to be equal to 15.

Based on the condition explained above for the width B, a radius R of the scattering cone of coherent scattered radiation at a point P, with a distance of $Z_P$ from the coordinate origin, is calculated as follows: $R=\beta*Z_P$. If one uses the formula indicated above for $\beta$, then this yields $R=2*q_{max}*\lambda*Z_P$. In order to obtain a resolution of 5% in the diffraction pattern, which corresponds to a value of $dq/q_{max}=0.05$, the height h of each detector element must be less than or equal to 0.05*R. This yields the relation $h=0.1*q_{max}*\lambda*Z_P$. This applies to the small angle approximation. An example for a value of h is 2.5 mm if one assumes normal values such as $q_{max}=2$ nm$^{-1}$, $\lambda=1.24*10_{-2}$ nm (corresponds to 100 keV), and $Z_P=1,000$ mm.

With the above-mentioned prerequisites, the only material that contributes to the coherent scattered signal in a specific detector element is that which is situated in the region of the scattering voxel S. Simulation calculations have established that although a multitude of different contributors do in fact contribute to the overall scattered signal, in the range of low pulse transmissions q, the coherent scattering predominates. This is because electron-binding effects suppress the single Compton signal, while the multiple Compton signals constitute a structureless background that can often be approximated by means of a constant.

FIG. 2 schematically depicts how the x-ray source 1 and the detector array 5 are attached to a gantry (not shown) that can be rotated around the test piece 4. The region of the test piece 4 that an individual detector element of the detector array 5 "sees" is clearly visible in this figure. By contrast with the situation in FIG. 1, in this case the gantry is rotated by an imaging angle φ around an axis parallel to the y axis. The detector array 5 takes a reading for each value of the imaging angle φ so that for each imaging angle X, a four-dimensional data set is generated, In addition to the imaging angle φ. This data set $S_{raw}$ (φ,E, x, y) [depends] also on the energy E of the x-ray quantum that is detected in the energy-resolving detector element as well as the x and y coordinates of the detector element that performs the detection.

The section below will describe a method with which the four-dimensional scattered data obtained can be used to deduce what material is contained in the test piece 4 at each individual scattering voxel S. First, an energy calibration must be performed on the system. This is followed by the subtraction of the multiple scattering components from the scattered signal detected. Then the scattered signal is scaled to the transmission component. Based on the above-mentioned raw data $S_{raw}$, this yields the corrected scattered data S (φ, E, x, y) of the scattered signal. Such methods are known from the literature and are referred to as algebraic reconstruction techniques (ART).

The second step requires an estimation of the multiple scattering component. This can be derived from measurements or photon transport simulations with typical test piece geometries. It is also possible to formulate this second step in the iterative construction by estimating the multiple scattering component, which is based on the current object distribution. In ART, forward projection data that result from an assumed material distribution with a known molecular structure function are compared to the measured scattered data. The deviations between these two data sets are subjected to iterative back projections into the object space.

Data of the back projection of the data S (φ$_1$, E$_1$, x$_1$, y$_1$) from the first projection into the object space are inserted into an object matrix $\sigma_{mol}$, taking into account the geometric assumptions. With a static image grid, the rotation of the system comprised of the x-ray source 1 and detector array 5 is simulated, with the angular steps that were executed during the measurement. A forward projection is then performed using the values of the object matrix $\sigma_{mol}$ from the first step, The difference between the forward projection data and the measured data is inserted into a difference matrix that is then used for a back projection. Repeated iterative forward and back projections are performed until the imaging data have all been used once, This procedure is repeated several times, with the weighting being reduced each time until the average quadratic error sum of the difference matrix is no longer reduced in the subsequent iteration step.

REFERENCE NUMERAL LIST 1 x-ray source
2 fan beam
3 line of sight
4 test piece
5 detector array
6 primary radiation element
7 secondary radiation element
8 observation region
B width of a detector element
h height of a detector element
P observation point
S scattering voxel
R radius
φ imaging angle

The invention claimed is:

1. An x-ray computer tomograph, comprising:
   an x-ray source configured to generate a fan beam of x-ray radiation;
   a detector array, wherein each of the x-ray source and the detector array is situated on opposite sides of a gantry so that the x-ray radiation passes completely through a test region;
   a row of detector elements situated in a plane of the fan beam and adjoined in at least one direction perpendicular to the fan beam by several additional rows of detector elements;
   wherein during a measurement, no secondary collimator is positioned between the test region and the detector array,
   wherein a width of each of the detector elements is less than or equal to $0.5*\beta*Z_P$, where β is twice the angle of spread of the x radiation and $Z_P$ is the distance of the measurement point from the detector array, and
   wherein a height (h) of each of the detector elements corresponds to the equation:

$h \leq 0.2* \arcsin(q*\lambda)*Z_P$, where q is a pulse transmission, λ is a wavelength of the x-ray radiation, and a pulse transmission spectrum lies between 0.2 and 2 nm$^{-1}$.

2. The x-ray computer tomograph as recited in claim 1, wherein an energy of the x-ray radiation lies between 100 KeV and 500 keV.

3. The x-ray computer tomograph as recited in claim 1, wherein the detector array is situated on a circumference surface of a cylinder around a center axis extending through the x-ray source, perpendicular to the fan beam.

4. The x-ray computer tomograph as recited in claim 1, wherein the detector array is a pixilated detector array, which is equipped with from 5 to 50 detector elements in a y-direction.

5. The system of claim 1, wherein the detector array is a two-dimensional energy-resolving detector array.

6. A method for examining a test piece by means of an x-ray computer tomograph, the method comprising:
   performing a locally resolved measurement of coherent x-ray radiation scattered forward by the test piece without a secondary collimator being positioned between the test piece and a detector array,
   wherein a width of each detector element in the detector array is less than or equal to $0.5*\beta*Z_P$, where β is twice an angle of beam spread of the x-ray radiation and $Z_P$ is a distance of a scattering point from the detector array, and wherein a height (h) of each detector element corresponds to the equation:

$$h \leq 0.2 * \arcsin(q*\lambda)*Z_P,$$

where q is a pulse transmission, $\lambda$ is a wavelength of the x-ray radiation, and a pulse transmission spectrum lies between 0.2 and 2 $nm^{-1}$.

7. The method as recited in claim 6, further comprising in order to record scattered data: rotating the gantry around an axis that is perpendicular to a plane of the fan beam.

8. The method as recited in claim 6, further comprising:
inserting a forward-projected scattered signal and a measured scattered signal into a difference matrix; and
repeating forward and back projections until all projection data have been used once.

9. The method as recited in claim 8, wherein the forward and back projections are repeated with reduced weighting until a sum of average quadratic errors of the difference matrix no longer decreases.

* * * * *